US00PP10522P

United States Patent [19]

Van Antwerp

[11] Patent Number: Plant 10,522

[45] Date of Patent: Jul. 28, 1998

[54] *TERNSTROEMIA GYMNANTHERA* 'GREVAN'

[75] Inventor: Jim Van Antwerp, Grand Bay, Ala.

[73] Assignee: Greenleaf Nursery Company, Park Hill, Okla.

[21] Appl. No.: 759,557

[22] Filed: Dec. 4, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Synnestvedt & Lechner

[57] ABSTRACT

A new variety of Japanese Ternstroemia plant, *Ternstroemia gymnanthera* 'Grevan', which is particularly characterized by its compact, mounding-spreading, and symmetrical growth habit, and which is distinguishable from standard Japanese Ternstroemia plants which demonstrate an upright-oval growth habit and irregular branching habit.

7 Drawing Sheets

BACKGROUND OF THE NEW PLANT

The present invention relates to the discovery and asexual propagation of a new and distinct cultivar of *Ternstroemia qymnanthera*, a member of the Theaceae family that is commonly known as Japanese Ternstroemia, and often referred to as Cleyera. The new variety of *Ternstroemia gymnanthera* has been given the cultivar name 'Grevan'.

The new variety was discovered by Jim Van Antwerp in the summer of 1991, amongst a cultivated planting of seedling Japanese Ternstroemia plants at Greenleaf Nursery in El Campo, Tex. The parent variety of Japanese Ternstroemia is unknown, as there is currently only one other named cultivar, *Ternstroemia gymnanthera* 'Variegata', in horticultural literature. The parent species is referred to herein as "standard" or "traditional" Japanese Ternstroemia.

The new 'Grevan' plant was recognized as being very different in appearance from traditional Japanese Ternstroemia plants, and was particularly selected for its unique, compact form and growth habit that is more spreading than that of the parent species. The botanical characteristics of the new 'Grevan' variety are substantially the same as the parent species, but for those characteristics contributing to the new plant's appearance, namely, the smaller and narrow elliptic-shaped leaves and the distinctive compact, mounding and symmetrical growth habit exhibited by the 'Grevan' plants. The dense, self-branched growth habit and low profile of the new 'Grevan' variety give it several desirable characteristics for ornamental landscape use. The new variety is readily distinguishable from traditional or standard Japanese Ternstroemia plants, which demonstrate an upright-oval growth habit and an irregular branching habit.

The new 'Grevan' variety was first asexually propagated by Jim Van Antwerp in the summer of 1991 at the same nursery in which it was discovered. The new variety has shown to be stable in its distinguishing characteristics over several generations, through successive asexual propagations using vegetative cuttings.

BRIEF DESCRIPTION OF THE DRAWINGS

The accompanying photographic drawings illustrate in color the 'Grevan' cultivar as grown in a nursery in El Campo, Tex., and also show the comparison between the new 'Grevan' variety and the parent species, as well as the coloration of new and mature foliage on both the new and parent plants. Except as noted, the photographs are of plants grown outdoors and in containers above ground.

DETAILED DESCRIPTION OF THE NEW PLANT

Figure 1:
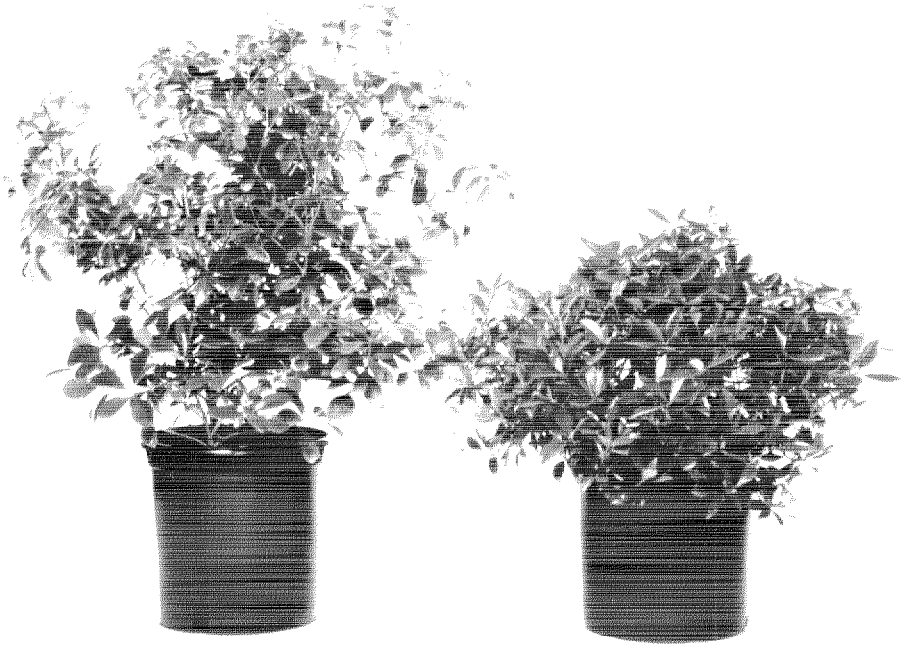
FIG. 1 shows a comparison between a traditional Japanese Ternstroemia plant (left) and the new 'Grevan' variety (right) in the spring. The two plants were grown under culturally identical conditions; however, the standard variety received shearings to improve fullness and structure while the new 'Grevan' variety received no shearing. Both plants are about three years old and were grown from cuttings.
Figure 2:
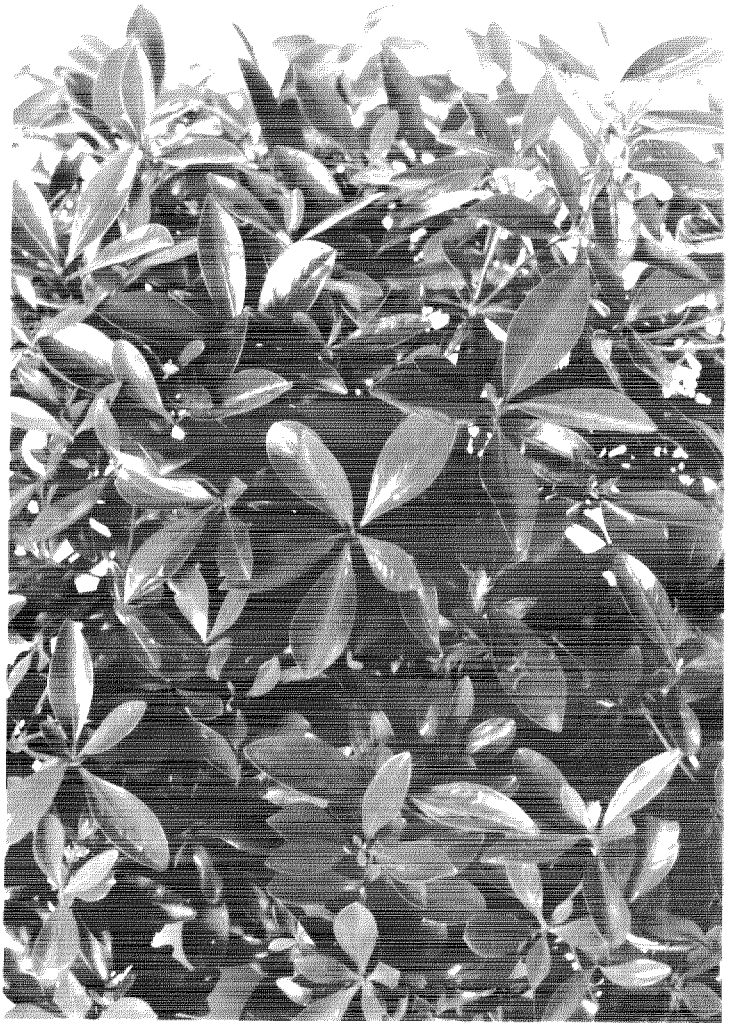
FIG. 2 shows the foliage of the new 'Grevan' variety.
Figure 3:
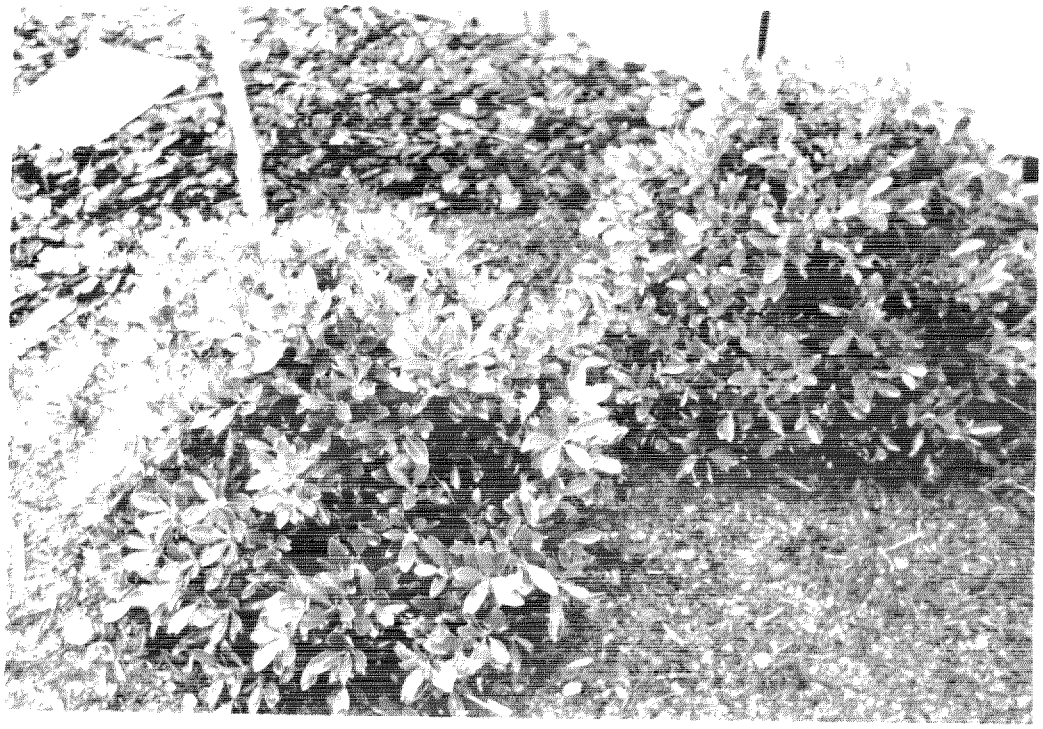
FIG. 3 shows a one year old landscape planting of two 'Grevan' plants.
Figure 4:
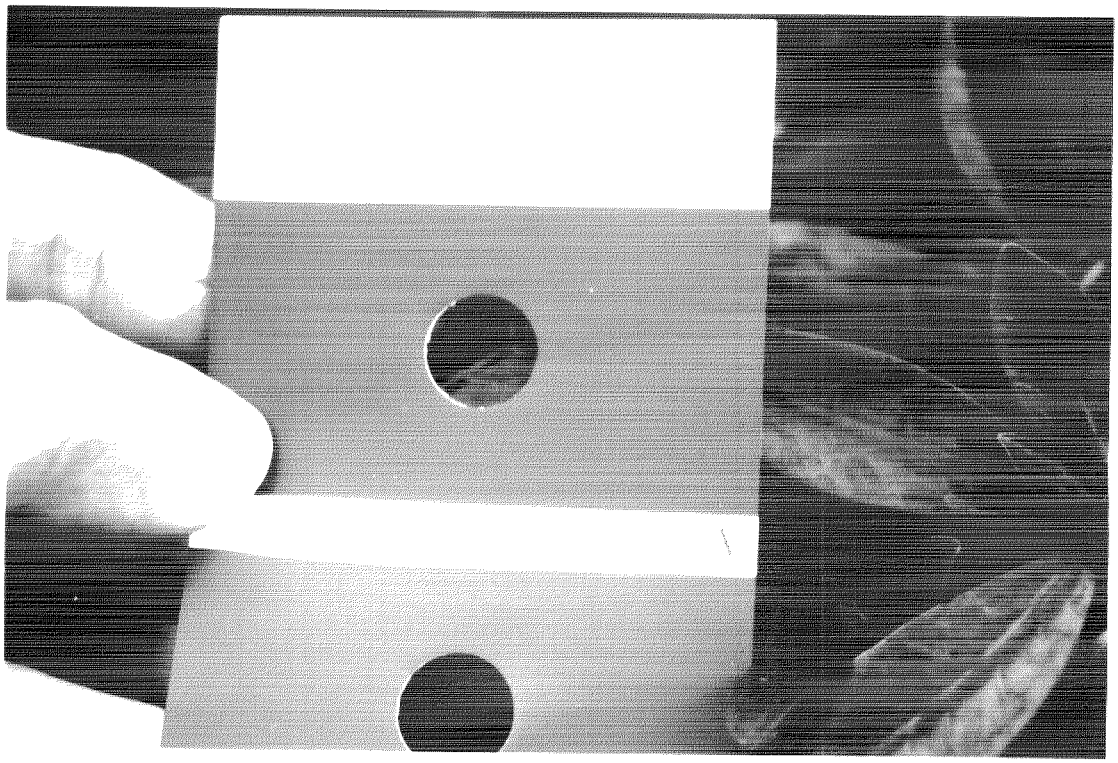
FIG. 4 shows the top side of immature foliage of the new 'Grevan' variety, superimposed by the matching R.H.S. color card of the Yellow-Green Group.
Figure 5:
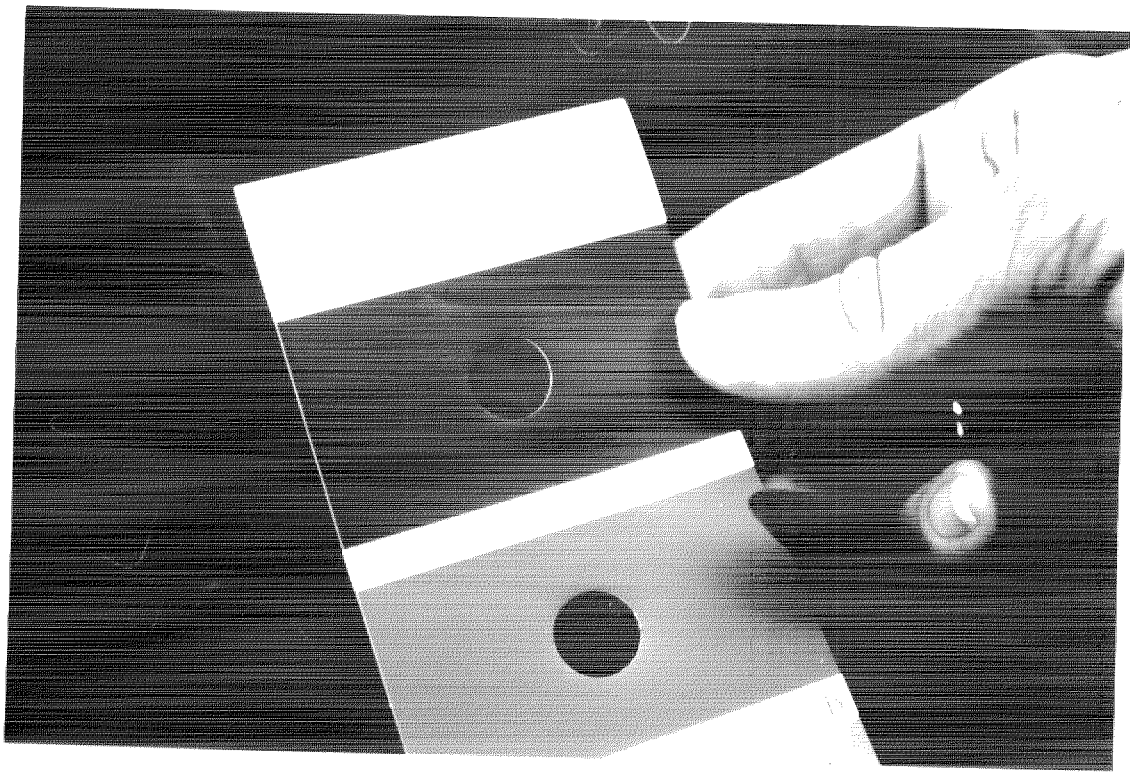
FIG. 5 shows the top side of mature foliage of the new 'Grevan' variety, superimposed by the matching R.H.S. color card of the Yellow-Green Group.
Figure 6:
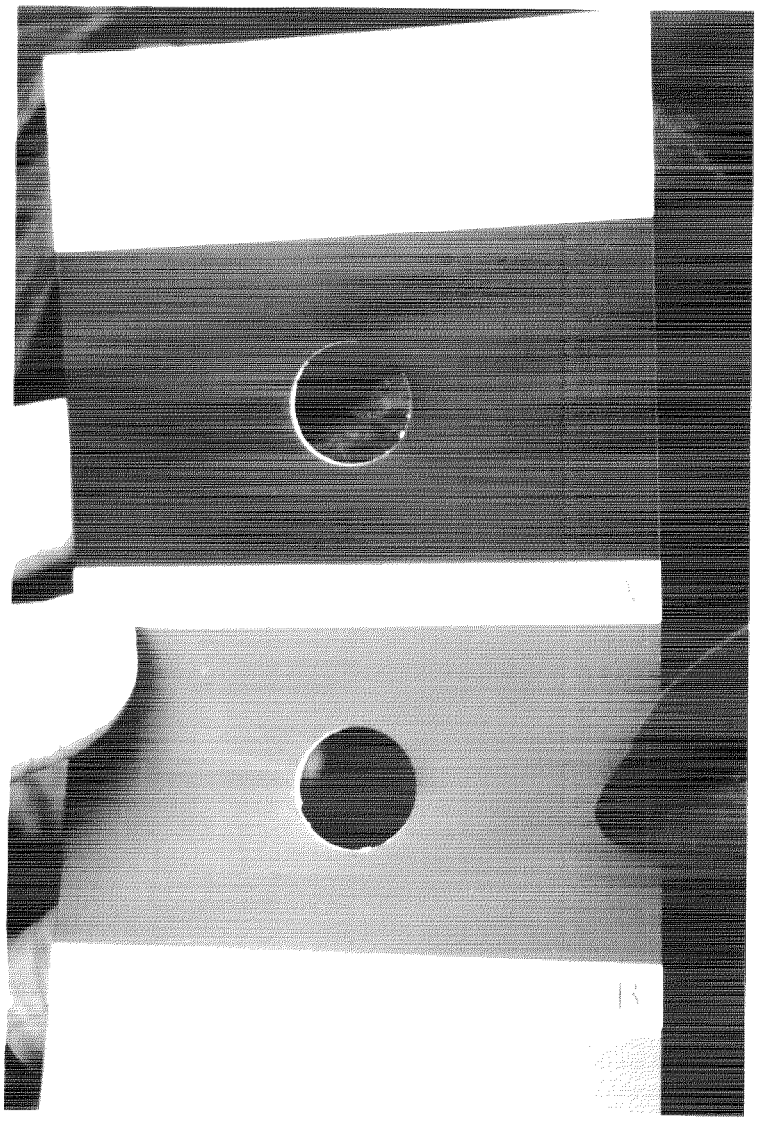
FIG. 6 shows the top side of immature foliage of a traditional Japanese Ternstroemia plant, superimposed by the matching R.H.S. color card of the Greyed-Orange Group.
Figure 7:
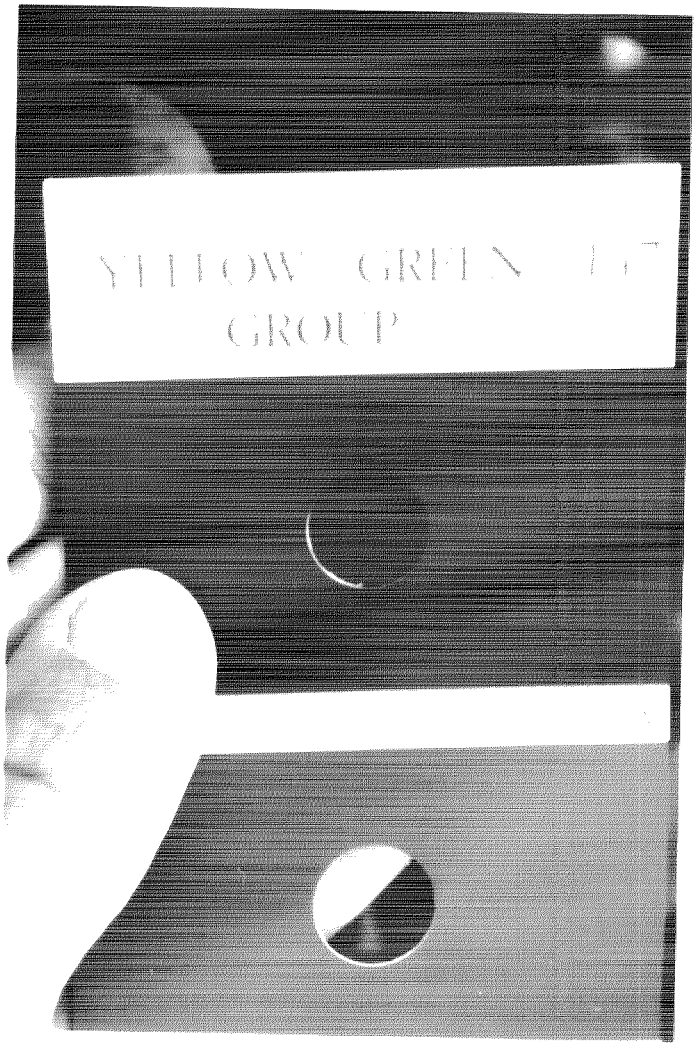
FIG. 7 shows the top side of mature foliage of a traditional Japanese Ternstroemia plant, superimposed by the matching R.H.S. color card of the Yellow-Green Group.

The following detailed description of the new *Ternstroemia gymnanthera* 'Grevan' plant is based upon observations made of the plants grown under commercial, wholesale nursery production practices and in landscape plantings in El Campo, Tex. It is believed that this description will apply to 'Grevan' cultivar plants grown in similar conditions of soil and climate elsewhere.

Throughout this specification, color names beginning with a small letter signify that the name of that color as used in common speech is aptly descriptive. Color names beginning with a capital letter designate color values based on the R.H.S. Colour Chart published by The Royal Horticultural Society of London, England.

Name: *Ternstroemia gymnanthera* 'Grevan'.

Origin: Seedling of unknown parentage.

Parentage: Unknown variety of *Ternstroemia gymnanthera* plants.

Hardiness: USDA Zone 7; typical of the species.

Growth Habit: Compact/dense; self-branching; symmetrical; more spreading than that of the parent species.

Texture: Medium; more compact and denser of branching and canopy than that of the parent species.

Size: Mature height is anticipated to be about 100–120 cm. with a width of about 100–120 cm. This is typically shorter and proportionally wider than the species as a function of lesser terminal growth and denser branching as compared to the species.

Foliage:

*Type.*—Evergreen.

*Arrangement.*—Irregularly, spirally arranged around the apical end of the stem of each growth flush. The lower end of each stem is leafless with widely spaced blind leaf nodes. Leaf and blind leaf node spacing is similarly irregular on the 'Grevan' variety and the parent species. The number of branches per growth flush vary from about 1 to 7, which is similar to the parent species. However, the length of each growth flush is shorter than (about 30–50% as long as) the growth flushes of the parent species, thereby giving the plant a fuller appearance.

*Leaf insertion.*—Petiolate.

*Petiole.*—Length: about 4–6 mm. (parent species about 4–6 mm.) Thickness: about 2 mm. (parent species about 2 mm.) Color: above: Red 46A (parent species Red 46A). below: Yellow-Green 146D (parent species Red 46A fading with age to Yellow-Green 146D). The color on the underside of the young petiole of the parent species fades quickly with age from Red 46A to Yellow-Green 146D. The red pigment of the top side of the petiole of both plants also fades with age, but persists about one (1) year longer than the underside pigment.

*Leaf shape.*—Narrow elliptic.

*Leaf tip.*—Acute.

*Leaf base.*—Narrow attenuate.

*Leaf margin.*—Entire.

*Leaf venation.*—Pinnate.

*Leaf surface above.*—Lustrous, leathery.

*Leaf surface below.*—Glabrous, leathery.

*Mature leaf length.*—Shorter than parent species; about 45–60 mm.

*Mature leaf width.*—Narrower than parent species; about 10–20 mm.

Bark: Typical of the species; no noticeable difference in color or appearance of bark of more recent growth; bark color darkens with age, staring and varying within the Greyed-Green Group (197) and eventually darkening to the Brown Group (200); the bark starts smooth and roughens slightly with age, but has not been observed to fissure or exfoliate.

Flowers: Color and size typical of the species; white to cream in color, perfect, borne singly on about 10–15 mm. cream peduncle emerging from leaf axils and blind leaf nodes; flowers about 8–10 mm. wide; flowers observed October/November, contrary to literature which refers to flowers observed in May/June.

Fruit: None observed to date, but expected to be typical of the species.

Color:

TABLE 1

| | 'Grevan' | Standard Japanese Ternstroemia |
|---|---|---|
| New Foliage --Top: | Yellow-Green 152A | Greyed-Orange 166A |
| New Foliage --Bottom: | Yellow-Green 146C | Yellow-Green 146D |
| Mature Foliage --Top: | Yellow-Green 147A | Yellow-Green 147A |
| Mature Foliage --Bottom: | Yellow-Green 146B | Yellow-Green 147C |
| Mature Stem: | Brown 200D | Brown 200B |

I claim:

1. A new and distinct cultivar of *Ternstroemia gymnanthera* plant named 'Grevan', as herein illustrated and described.

* * * * *